US006127112A

United States Patent [19]

Velicer et al.

[11] Patent Number: 6,127,112

[45] Date of Patent: Oct. 3, 2000

[54] AVIAN HERPESVIRUS-A ANTIGEN PRECURSOR GENE

[75] Inventors: Leland F. Velicer, East Lansing, Mich.; Robert J. Isfort, Frederick, Md.; Hsing-Jien Kung, Solon, Ohio; Paul M. Coussens, DeWitt, Mich.

[73] Assignee: Board of Trustees operating Michigan State University, East Lansing, Mich.

[21] Appl. No.: 07/866,296

[22] Filed: Apr. 13, 1992

Related U.S. Application Data

[63] Continuation of application No. 07/526,790, May 17, 1990, abandoned, which is a continuation of application No. 07/041,974, Apr. 24, 1987, abandoned.

[51] Int. Cl.[7] .............................. C12Q 1/68; C12Q 1/70; C12N 15/85; C12N 7/04

[52] U.S. Cl. ............................... 435/5; 435/6; 435/320.1; 435/325; 435/349; 435/235.1; 435/236; 536/23.1; 536/23.72

[58] Field of Search ............................... 435/172.3, 69.1, 435/320.1, 5, 6, 325, 349, 235.1, 236; 536/27, 23.1, 23.72

[56] References Cited

PUBLICATIONS

Smith et. al., Mol. Cell. Biol., vol. 3, No. 12, Dec. 1983, pp. 2156–2165.
Pharmacia Catalog (1984) p. 58, 59.
Purchase, H.G., Beltsville Symp. Agri. Res. 1:63–81 (1977).
Okazaki, W., et al., Avian Dis. 14:413–429 (1970).
Ikuta, K., et al., J. Gen. Virol. 64:961–965 (1983).
Silva, R.F., et al., Virology 136; 307–320 (1984).
Glaubiger, C., et al., J. Virol. 45:1228–1234 (1983).
(a) Long, et al., J. Virol. 15:1182–1192 (1975).
(b) Long, et al., J. Virol. 15:1192–1201 (1975).
Isfort, et al., J. Virol. 57:464–474 (1986).
Ikuta, et al., J. Gen. Virol. 64:2597–2610 (1983).
Nazerian, K., J. Gen. Virol. 21:193–195 (1973).
Payne, L.W., Biology of Marek's Disease virus and the herpesvirus of turkeys, pp. 347–431, In B. Roizman (ed.) The herpesviruses, vol. I (1982).
Wainberg, M.A., B. Beiss, and E. Israel, Avian Dis. 24:580–590 (1980).
Isfort, et al., p. 130–147, Proc. Int. Symp. Marek's Dis./The American Assoc. of Avian Path., Inc. Kennett Sq. PA (1985).
Gibbs, et al., Proc. Natl. Acad. Sci. USA 81:3365–3369 (1984).
Fukuchi, et at. J. Virol. 51: 102–109 (1984).
Maniatis, et al., Molecular cloning. Cold Spring Harbor Lab, Cold Spring Harbor, NY (1982).
Parnes et al., Proc. Natl. Acad. Sci. USA 78: 2253–2257 (1981).
Southern, E.M., J. Mol. Biol. 98:503–517 (1975).
Rigby, et al., J. Mol. Biol. 113;237–251 (1977).
Favaloro, et al., Meth. Enzymol. 65:718–749 (1980).
Paterson, et al., Proc. Natl. Acad. Sci. USA 74:4370–4374 (1977).
Jackson et al., Meth. Enzymol.96:50–74 (1983).
Lehrach, et al., Biochemistry 16:4743–4751 (1977).
Witte, et al., J. Virol. 29: 735–743 (1979).
Laemmli, U.K., Nature 227: 680–685 (1970).
Weber et al., J. Biol. Chem. 244:4405–4412 (1969).
Bonner, et al., Eur. J. Biochem. 46:83–88 (1974).
Hughes, et al., Virology 105:234–240 (1980).

*Primary Examiner*—David Guzo
*Attorney, Agent, or Firm*—Ian C. McLeod

[57] ABSTRACT

A gene encoding for A antigen precursor, derived from a Avian herpesvirus, is described. The gene is preferably isolated from a Marek's disease herpesvirus virus (MDHV) and is approximately 1.8–1.9 kbp, found on a DNA fragment of about 2.35 kbp in size. The gene can be used as a building block for vaccines, directly as a diagnostic hybridization probe, to facilitate preparation of diagnostic test kits for MDHV by antigen production and subsequent antibody production, and as a potential source of regulatory elements such as signal peptides or promoters for use with other proteins.

8 Claims, 5 Drawing Sheets

HYBRID-SELECTION OF MDHV-A mRNA WITH INDIVIDUAL DNA CLONES FOLLOWED BY CELL-FREE TRANSLATION

FURTHER ANALYSIS OF THE CLONE THAT SELECTS MDHV-A mRNA

A. MAP OF pBR328 MDHV CLONE #15

B. HYBRID-SELECTION OF RNA FOR CELL-FREE TRANSLATION USING FRAGMENTS OF pBR328, RαA IMMUNOPRECIPITATION

LOCALIZATION OF THE MDHV-A GENE IN THE BAM HI B FRAGMENT BY SOUTHERN BLOT HYBRIDIZATION AND BY NORTHERN BLOT AND HYBRID-SELECTION ANALYSIS

Region of homology between the MDHV Bam HI B fragment and the 2.35 kbp fragment from the Eco RI pBR328 library

NORTHERN BLOT
ANALYSIS OF
INFECTED CELL RNA

AVIAN HERPESVIRUS-A ANTIGEN PRECURSOR GENE

This is a continuation of application Ser. No. 07/526,790 filed on May 17, 1990, now abandoned, which is a continuation of application Ser. No. 07/041,974, filed Apr. 24, 1987, now abandoned.

BACKGROUND OF THE INVENTION (1) Field of the Invention

The present invention relates to a substantially pure fragment of an Avian herpesvirus genome containing the gene for A antigen precursor polypeptide pr47 or a subfragment thereof which is the unglycosylated precursor to A antigen (gp57–65). In particular the present invention relates to an about 2.35 kbp fragment or subfragment of DNA from a Marek's disease herpesvirus which contains the gene that encodes for A antigen precursor pr47.

(2) Prior Art

Marek's disease (MD) is a lymphoproliferative disease of chickens caused by Marek's disease herpesvirus (MDHV), which results in T-cell lymphomas and peripheral nerve demylination (Marek, J., Multiple Nervenetzuendung (Polyneuritis) bei Huchnern. Dtsch. Tieraerztl. Wochenschr. 15:417–421 (1907); Pappenheimer, A. M., L. C. Dunn, and V. Cane, J. Exp. Med. 49:63–86 (1929); and Pappenheimer, A. M., L. C. Dunn, and S. M. Seidlin, J. Exp. Med. 49:87–102 (1929)). The disease was a major cause of economic loss ($200 million/year) to the poultry industry until the early 1970's (Purchase, H. G., Beltsville Symp. Agri. Res. 1:63–81 (1977)), when a live vaccine was developed from the antigenically related apathogenic herpesvirus of turkey (HVT) (Okazaki, W., H. G. Purchase, and B. R. Burmester, Avian Dis. 14:413–429 (1970)).

The ability of HVT to protect chickens against infection by MDHV may be due to an antigenic relationship between HVT and MDHV. At least six antigenically active viral proteins are common between MDHV and HVT (Ikuta, K. S., S. Ueda, S. Kato, and K. Hirai, J. Gen Virol. 64:961–965 (1983); and Silva, R. F., and L. F. Lee, Virology 136-307-320 (1984)). One of these antigenic proteins, the prominent MDHV A antigen (MDHV-A), was the first MDHV-HVT common antigen to be characterized on a physical, chemical and molecular basis (Glaubiger, C., K. Nazerian, and L. F. Velicer., J. Virol. 45:1228–1234 (1983); Long, P. A., K. Y. Parveneh, and L. F. Velicer, J. Virol. 15:1182–1192 (1975); and Long, P. A., J. L. Clark, and L. F. Velicer, J. Virol. 15:1192–1201 (1975)). MDHV-A is a glycoprotein with an apparent molecular weight of 57–65,000 daltons referred to as (gp57–65) in its fully glycosylated form (Glaubiger, C., K. Nazerian, and L. F. Velicer, J. Virol. 45:1228–1234 (1983); and Isfort, R. J., R. A. Stringer, H. J. Kung, and L. F. Velicer, J. Virol. 57:464–474 (1986)). A combination of cell-free translation, pulse-chase, and tunicamycin inhibitor studies have shown that MDHV-A is synthesized as a 47,000 dalton precursor polypeptide that apparently undergoes cleavage to remove a small signal peptide (Isfort, R. J., R. A. Stringer, H. J. Kung, and L. F. Velicer, J. Virol. 57:464–474 (1986)). The resulting 44,000 dalton polypeptide undergoes glycosylation and secretion from the cell in a precisely programmed manner (Isfort, R. J., R. A. Stringer, H. J. Kung, and L. F. Velicer, J. Virol. 57:464–474 (1986)). While MDHV-A is primarily secreted from infected cells (Isfort, R. J., R. A. Stringer, H. J. Kung, and L. F. Velicer, J. Virol. 57:464–474 (1986)), there is mounting evidence that a small amount is also associated with the plasma membrane in a specific manner (Ikuta, K. S., S. Ueda, S. Kato, and K. Hirai, J. Gen. Virol. 64:2597–2610 (1983); Nazerian, K., J. Gen. Virol. 21:193–195 (1973)). Not only is its role in the immunoprevention by HVT still unclear, it could have a role in the pathogenesis of MD since it has been recently postulated to play an immunoevasive role in protecting virus-producing cells of the feather follicle epithelium (Isfort, R. J., R. A. Stringer, H. J. Kung, and L. F. Velicer, J. Virol. 57:464–474 (1986)). Furthermore any virus-encoded glycoprotein should be a candidate for causing the early stage immunosuppression that is reported to occur after MDHV infection and may be one of the key events that lead to neoplasia (Payne, L. W., Biology of Marek's disease virus and the herpesvirus of turkeys, pp. 347–431. In B. Roizman (ed.), The herpesviruses, vol. 1. Plenum Press (1982)); especially in view of the observation that various virus particles, either infectious or non-infectious, inhibit mitogenic responses (Wainberg, M. A., B. Beiss, and E. Israel, Avian Dis. 24:580–590 (1980)).

OBJECTS

It is an object of the present invention to provide the gene that encodes for the precursor protein of antigen MDHV-A. It is further an object of the present invention to provide the gene for further molecular characterization of the protein, and for producing expression products of the MDHV-A gene in order to better assess its role(s) in the immunosuppression, immunoevasion and/or immunoprotection processes. These and other objects will become increasingly apparent by reference to the following description and the drawings.

BRIEF DESCRIPTION OF THE DRAWINGS

FIG. 1A shows a direct analysis of the products of MDHV-specific mRNAs that were hybrid-selected and cell-free translated. Lanes 1–15 show translation of cytoplasmic RNA isolated 72 hours post infection (PI) from MDHV-infected cells and selected using pBR328 clones 1–15; lane 16 (INF) shows translation of unselected cytoplasmic RNA isolated 72 hours PI from MDHV-infected DEF; lane 17 (CON) shows translation of unselected cytoplasmic RNA isolated from uninfected DEF; lane 18 (RNA) shows translation with no added RNA. Ten microliters of each translation mixture was analyzed per lane to display all the polypepetides produced. Samples were analyzed on 10% SDS-PAGE and the autoradiogram of the dried gel was prepared by fluorographic exposure for 2 days. FIG. 1B shows immunoprecipitation and SDS-PAGE analysis of the products of hybrid-selected and cell-free translated MDHV specific mRNAs. Lanes 1–17 of FIG. 1B are the same as in A, but the translation products were immunoprecipitated with RαA sera. Forty microliters of each translation reaction mixture was subjected to immunoprecipitation with 2 microliters of RαA. Samples were analyzed on 10% SDS-PAGE, and the autoradiogram of the dried gel was prepared by fluorographic exposure for 5 days. Clone 15 is the only one to hybrid-select.

FIG. 2A shows a restriction map of pBR328-15. FIG. 2B shows cell-free translation using subfragments of pBR328-15 followed by immunoprecipitation with RαA sera. Hybrid-selections, cell-free translation, immunoprecipitation, SDS-PAGE and fluorography were performed as in FIG. 1, with fluorographic exposures for 7 days. Only the 2.35 kbp fragment hybrid-selects the messenger RNA encoding for A antigen.

GENERAL DESCRIPTION

Figure 1A:
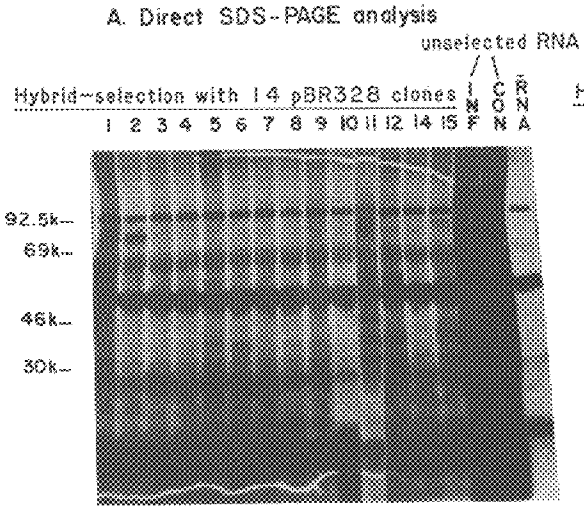
FIGS. 1A and 1B show a SDS-PAGE analysis of cell-free translation products of mRNA hybrid-selected using 14 individual pBR328 MDHV DNA clones immobilized on nitrocellulose.

The present invention relates to a substantially pure Eco$R_1$-PvuII endonuclease digestion gene-containing fragment of an Avian herpesvirus genome containing the gene for A antigen precursor polypeptide and a subfragment of the fragment.

The present invention also relates to a method for removing the gene coding for A antigen from DNA of an Avian herpesvirus which comprises: digesting the herpesvirus DNA or a fraction thereof with Eco$R_1$-PuvII endonucleases to provide a segment which contains the gene for A antigen.

The gene encoding the glycoprotein MDHV-A antigen's unglycosylated precursor polypeptide pr47 was delineated using Northern blot analysis and hybrid-selection of its mRNA with cloned MDHV DNA, cell free translation of the mRNA and immunoprecipitation of the polypeptide. The resulting piece of DNA with strongly positive hybrid-selection results was the 2.35 kbp Pvu II-EcoRI restriction fragment localized to the center of the 18.3 kbp MDHV Bam HI B fragment of the total virus genome. The much lower level of hybrid-selection and detection of mRNA in Northern blot analysis by the adjacent 2.4 kbp ECO RI-Sma I fragment initially suggested it may contain a very small part of the MDHV-A gene, if any at all. It is now clear that the 3' end of the gene for MDHV-A is within the 2.35 kbp fragment, suggesting these borderline results are due to read-through transcription to yield a small amount of large mRNA spanning the junction between the two fragments. The localization was specific since no other small restriction subfragment of the larger BAM HI B fragment was able to hybrid-select MDHV-A mRNA and the gene mapped only in the Bam HI B fragment of the total virus genome. Northern blot analysis confirmed the localization of the MDHV-A gene primarily on the 2.35 kbp fragment and detected its mRNA as a 1.8 k daltons species, a size consistent with encoding a 47 kd polypeptide. This then is the first disclosure of a MDHV gene being mapped to the MDHV viral genome. This development opens the way for the use of recombinant DNA technology to study the nature of the gene encoding a secreted virus-specific glycoprotein that could possibly be involved in immunoprevention, immunosuppression and/or immunoevasion, immune phenomena known or speculated to be involved in this oncogenic herpesvirus system.

SPECIFIC DESCRIPTION

MATERIALS AND METHODS

Cells and viruses. The preparation, propagation and infection of small scale duck embryo fibroblast (DEF) cell culture with MDHV was generally as first reported by Glaubiger et al. (Glaubiger, C., K. Nazerian, and L. F. Velicer, J. Virol. 45: 1228–1234 (1983) and more recently by Isfort et al (Isfort, R. J., R. A. Stringer, H. J. Kung and L. F. Velicer, J. Virol. 57:464–474 (1986). One exception was that 0.2% calf serum was present in the maintenance media, as previously reported (Isfort, R. J., R. A. Vrable, K. Nazerian, J. J. Kung and L. F. Velicer, Gene identification and molecular characterization of the Marek's disease virus A antigen, p. 130–147. In B. W. Calnek and J. L. Spencer (eds.), Proc. Int. Symp. Marek's Dis. The American Association of Avian Pathologists, Inc., Kennett Square, Pa. (1985)). MDHV strain GA (Long, P. A., J. L. Clark, and L. F. Velicer, J. Virol. 15:1192–1201 (1975)) was used at the 26th passage level.

DNA preparation, gel electrophoresis and Southern blotting. MDHV DNA in the form of 14 pBR328 and 14 lambda clones was a gift from Dr. C. Gibbs (Gibbs, C., K. Nazerian, L. F. Velicer, and H. J. Kung, Proc. Natl. Acad. Sci. USA 81:3365–3369 (1984), currently at Rockefeller University. The MDHV Bam Hl library was a gift from Dr. M. Nonoyama, Showa University Research Institute (Fukuchi, K., M. Sudo, Y.-S. Lee, A. Tanaka, and M. Nonoyama., J. Virol. 51:102–1009 (1984)). The MDHV DNA in each clone was propagated in bacteria and then extracted by standard methods (Maniatis, T., E. Fritsch, and J. Sambrook., Molecular cloning. Cold Spring Harbor Laboratory, Cold Spring Harbor, N.Y. (1982)). The DNA (1 microgram from each clone) was bound to nitrocellulose for hybrid-selection using the method of Parnes et al (Parnes, J. R., B. Velan, A. Felsenfeld, L. Ramanathan, V. Ferrini, E. Apellka, and J. G. Seidman, Proc. Natl. Acad. Sci. USA 78:2253–2257 (1981)).

For further analysis, the entire MDHV genome, clone pBR328-15 and the MDHV Bam Hl clone B were digested with the appropriate restriction enzyme(s) using the conditions recommended by the manufacturer (Bethesda Research Laboratories located in Gaithersburg, Md.). The digests were then analyzed by gel electrophoresis at 4 volts/cm until the leading dye front was ¾ of the way down the gel. The gel was then stained in 0.5 ug/ml of ethidium bromide solution for 1 hour and photographed under ultraviolet light. Southern transfer of the electrophoresed DNA was performed according to the methods of Southern (Southern, E. M., J. Mol. Biol. 98:503–517 (1975)). Nick-translations of DNA fragments to be used as probes were performed according to the methods of Rigby et al (Rigby, P. W. J., M. Dieckmann, C. Rhodes, and P. Berg. J. Mol. Biol. 113-237-251 (1977)). Hybridization of the $^{32}P$-labeled probes to the nitrocellulose bound restriction fragments resulting from Southern blotting was performed according to the method of Maniatis et al. (Maniatis, T., E. Fritsch, and J. Sambrook, Molecular Cloning. Cold Spring Harbor Laboratory, Cold Spring Harbor, N.Y. (1982)).

Isolation of cellular RNA. The method of RNA isolation was that of Favaloro et al (Favaloro, J., R. Treisman, and K. Kamen., Meth. Enzymol. 65:718–749 (1980)). This method was modified so that the isolated RNA was not treated with DNase prior to the final ethanol precipitation step and the RNA was extracted five times with phenol/chloroform to remove all traces of vanadyl ribonucleotides (New England Nuclear located at Boston, Mass.).

Hybrid selection of MDHV specific mRNA. The method for hybrid-selection was that of Paterson et al (Paterson, B. M., B. E. Roberts, and E. L. Kuff., Proc. Natl. Acad. Sci. USA 74:4370–4374 (1977)), with the time of hybridization and the concentration of RNA modified to achieve maximal selection. Briefly, hybridization was carried out for 3 hours using 50 micrograms of total cellular RNA per filter in a 100 microliter volume.

Cell-free translation. Cell-free translation in rabbit reticulocyte lysates was performed using the methods of Jackson and Hunt (Jackson, R. J., and T. Hunt., Meth. Enzymol. 96:50–74 (1983)), as already reported in preliminary studies in the MDHV system (Isfort, R. J., R. A. Vrable, K. Nazerian, H. J. Kung, and L. F. Velicer., Gene identification and molecular characterization of the Marek's disease virus A antigen, p. 130–147. In B. W. Calnek and J. L. Spencer (eds.), Proc. Int. Symp. Marek's Dis. The American Association of Avian Pathologists, Inc., Kennett Square, Pa. (1985); and Isfort, R. J., R. A. Stringer, H. J. Kung, and L. F. Velicer, J. Virol. 57:464–474 (1986)). In the present invention translation after hybrid-selection was performed using the selected RNA with 10 micrograms of calf liver RNA added as carrier.

RNA gel electrophoresis and Northern blotting. Electrophoresis of RNA was performed according to the methods of Lehrach et al (Lehrach, E., D. Diamond, J. M. Wozney, and H. Boedtker., Biochemistry 16:4743–4751 (1977), as outlined by Maniatis et al (Maniatis, T., E. Fritsch, and J. Sambrook., Molecular cloning. Cold Spring Harbor Laboratory, Cold Spring Harbor, N.Y. (1982)). Northern blotting after electrophoresis was performed by transfer of formaldehyde-denatured RNA to nitrocellulose according to the method outlined by Maniatis et al (Maniatis, T., E. Fritsch, and J. Sambrook., Molecular Cloning. Cold Spring Harbor Laboratory, Cold Spring Harbor, N.Y. (1982)). Nick translation and hybridization with $^{32}P$ labeled probe was as described above for Southern blot analysis.

Immunoprecipitation with RαA. Immunoprecipitations were performed according to the methods of Witte and Wirth (Witte, O. N., and D. F. Wirth., J. Virol. 29:735–743 (1979)), as adopted to the MDHV system by Glaubiger et al (Glaubiger, C., K. Nazerian, and L. F. Velicer, J. Virol. 45:1228–1234 (1983) and used by Isfort et al (Isfort, R. J., R. A. Stringer, H. J. Kung, and L. F. Velicer., J. Virol. 57:464–474 (1986)). The RαA sera used to precipitate MDHV-A was prepared as previously described (Long, P. A., J. L. Clark, and L. F. Velicer, J. Virol. 15:1192–1201 (1975)) and has been used extensively for that purpose before (Glaubiger, C., K. Nazerian, and L. F. Velicer, J. Virol. 45:1228–1234 (1983); and Isfort, R. J., R. A. Stringer, H. J. Kung, and L. F. Velicer., J. Virol. 57:464–474 (1986)).

Sodium dodecyl sulfate-polyacrylamide gel electrophoresis (SDS-PAGE).

Discontinuous stack SDS-PAGE was performed according to the method of Laemmli (Laemmli, U.K., Nature 227:680–685 (1970)), as adapted to the MDHV system by Glaubiger et al (Glaubiger, C., K. Nazerian, and L. F. Velicer, J. Virol. 45:1228–1234 (1983)), with the previously reported modification (Isfort, R. J., R. A. Stringer, H. J. Kung, and L. F. Velicer, J. Virol. 57:464–474 (1986)): (1) all samples were boiled in sample buffer containing 2% SDS and 5% 2-mercaptoethanol prior to gel loading, (2) electrophoresis was carried out at a constant current of 30 mA until the marker dye ran off the gel. Standard molecular weight markers included $^{14}C$-labeled phosphorylase B (92.5 kd), bovine serum albumin (69 kd), ovalbumin (46 kd), and carbonic anhydrase (30 kd) (NEN). Molecular weights were calculated by interpolation between standard proteins by the method of Weber and Osborn (Weber, K., and M. Osborn, J. Biol. Chem. 244:4405–4412 (1969)). Fluorography was performed according to the methods of Bonner and Laskey (Bonner, W. M., and R. A. Laskey, Eur. J. Biochem. 46:83–88 (1974)). Autoradiography of all samples was carried out at −70° C.

RESULTS

In previous cell-free translation studies, it was established that the MDHV-A is synthesized as a 47,000 precursor polypeptide (pr47) immunoprecipitatable with RαA (Isfort, R. J., R. A. Stringer, H. J. Kung, and L. F. Velicer (J. Virol. 57:464–474 (1986)). Therefore, it was possible to combine hybrid-selection with these methods to identify the gene encoding MDHV-A from a partial genomic library of MDHV DNA (Gibbs, C., K. Nazerian, L. F. Velicer, and H. J. Kung, Proc. Natl. Acad. Sci. USA 81:3365–3369 (1984)).

Hybrid-selection was performed using RNA preparations isolated at the time of maximal A antigen synthesis (Isfort, R. J., R. A. Stringer, H. J. Kung, and L. F. Velicer (J. Virol. 57:464–474 (1986)). For the initial hybrid-selection, both the plasmid pBR328 and the lambda MDHV libraries were used (Gibbs, C., K. Nazerian, L. F. Velicer, and H. J. Kung, Proc. Natl. Acad. Sci. USA 81:3365–3369 (1984)). These libraries contain approximately 30% and 50% of the MDHV genome respectively (Gibbs, C., K. Nazerian, L. F. Velicer, and H. J. Kung, Proc. Natl. Acad. Sci. USA 81:3365–3369 (1984); C. Gibbs, unpublished data). Using DNA pools of either 14 MDHV pBR328 clones or 14 lambda MDHV clones, hybrid-selection was performed under stringent conditions of 65% formamide and 50° C. Washes to remove all non-hybridized RNA were performed at 65° C. and 0.15M sodium chloride. After direct SDS-PAGE analysis of the cell-free translation reaction mixture, approximately 18 to 20 proteins and 10 to 12 proteins, respectively, were produced by translation of mRNA selected by both the lambda and pBR328 cloned MDHV DNA pools (Isfort, R. J., R. A. Vrable, K. Nazerian, H. J. Kung and L. F. Velicer., Gene identification and Molecular characterization of the Marek's disease virus A antigen, p. 130–147. In B. W. Calnek and J. L. Spencer (eds.), Proc. Int. Symp. Marek's Dis. The American Association of Avian Pathologists, Inc., Kennett Square, Pa. (1985)). The background proteins made from uninfected DEF mRNA non-specifically binding to MDHV DNA was zero for the pBR328 clone pool. However, the lambda cloned DNA pool apparently selected mRNA for three DEF proteins (R. J. Isfort, unpublished data). This selection may result from the way the phage recombinant library was made. The pBR328 clones were constructed by cloning purified MDHV Eco Rl fragments (Gibbs, C., K. Nazerian, L. F. Velicer, and H. J. Kung., Proc. Natl. Acad. Sci. USA 81:3365–3369 (1984)), which results in no insertion of duck embryo fibroblast DNA sequences. However, the lambda clones were prepared by Mbo 1 partial digest of the MSB-1 chicken lymphoid tumor cell line (Hughes, S. H., E. Stubblefield, K. Nazerian, and H. E. Varmus, Virology 105:234–240 (1980)) DNA followed by insertion into the lambda cloning vector. Clones containing MDHV genome were selected using purified MDHV DNA as the hybridization probe (Gibbs, C., K. Nazerian, L. F. Velicer, and H. J. Kung., Proc. Natl. Acad. Sci. USA 81:3365–3369 (1984)). Since the library was constructed in this manner, any chicken cellular DNA next to integrated MDHV DNA (Hughes, S. H., E. Stubblefield, K. Nazerian, and H. E. Varmus, Virology 105:234–240 (1980)) may be carried into the lambda clone. This could result in hybrid-selection of DEF mRNA (homologous to the inserted chicken DNA) and subsequent translation of any protein encoded on the mRNA. Alternatively, the lambda clones may contain MDHV sequences sharing homology with the selected DEF mRNA. The absence of these background proteins, using mRNA selected by the pBR328 clones, may be due to either the incompleteness of the pBR328 MDHV library relative to the lambda library, or the lack of CEF sequences homologous to the DEF mRNA.

When these same cell-free translation reaction mixtures were analyzed by immunoprecipitation, MDHV-A's pr47 (Isfort, R. J., R. A. Stringer, H. J. Kung, and L. F. Velicer, J. Virol. 57:464–474 (1986)) was immunoprecipitated with the RαA sera from the two mixtures receiving infected cell RNA (Isfort, R. J., R. A. Vrable, K. Nazerian, J. J. Kung and L. F. Velicer, Gene identification and molecular characterization of the Marek's disease virus A antigen, p. 130–147. In B. W. Calnek and J. L. Spencer (eds.), Proc. Intl. Symp. Marek's Dis. The American Association of Avian Pathologists, Inc., Kennett Square, Pa. (1985)), indicating that the pBR328 and lambda cloned MDHV DNA pools both select a message encoding the MDHV-A polypeptide. The inability to visualize pr47 directly without immunoprecipitation analysis of the cell-free translation products is due to it comigrating with, and being obscured by, a background protein which migrates at the 40–50 kd region.

The above preliminary results indicate that both the pBR328 and lambda clones contain DNA sequences encoding for MDHV-A pr47. For further gene identification the 14 available MDHV pBR328 clones were used individually to hybrid-select the MDHV-A mRNA. The DNA of one clone, numbered 13 for identification in this study, was lost, explaining the gap in numbering of the clones. The direct SDS-PAGE analysis of the cell-free translated proteins whose mRNAs were hybrid-selected by DNA sequences contained in each clone is shown in FIG. 1A. At least 10–12 different proteins result from translation of mRNA selected by the 14 clones. One of the more interesting pBR328 clones is clone number 11 (pBR328-11), which selects mRNA encoding for at least nine different proteins. It should be noted that apparently many of the mRNAs selected for by pBR328-11 appear to be selected by other pBR328 MDHV clones (FIG. 1A), since similar proteins are seen in other lanes as well.

Figure 1B:
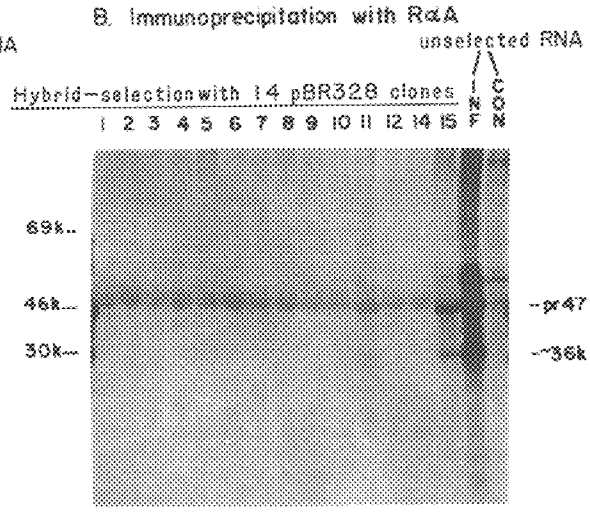

Immunoprecipitation analysis of these cell-free translation products with RαA showed that MDHV pBR328 clone number 15 (pBR328-15) contains a DNA sequence which selected for the mRNA of MDHV-A pr47 (FIG. 1B). Another polypeptide immunoprecipitable with RαA and migrating at about 30–36 kd in the same lane on the gel (FIG. 1B) may be either a product of premature translation termination, or a protein encoded by a transcript colinear with a portion of the MDHV-A mRNA and containing an antigenic domain recognizable by RαA. As already reported (Isfort, R. J., R. A. Vrable, K. Nazerian, H. J. Kung and L. F. Velicer. Gene identification and molecular characterization of the Marek's disease virus A antigen, p. 130–147. In B. W. Calnek and J. L. Spencer (eds.) Proc. Int. Symp. Marek's Dis. The American Association of Avian Pathologists, Inc., Kennett Square, Pa. (1985)), and will be seen in subsequent figures, this molecule is also made every time pr47 is synthesized by cell-free translation of MDHV-specific mRNA.

Figure 2A:
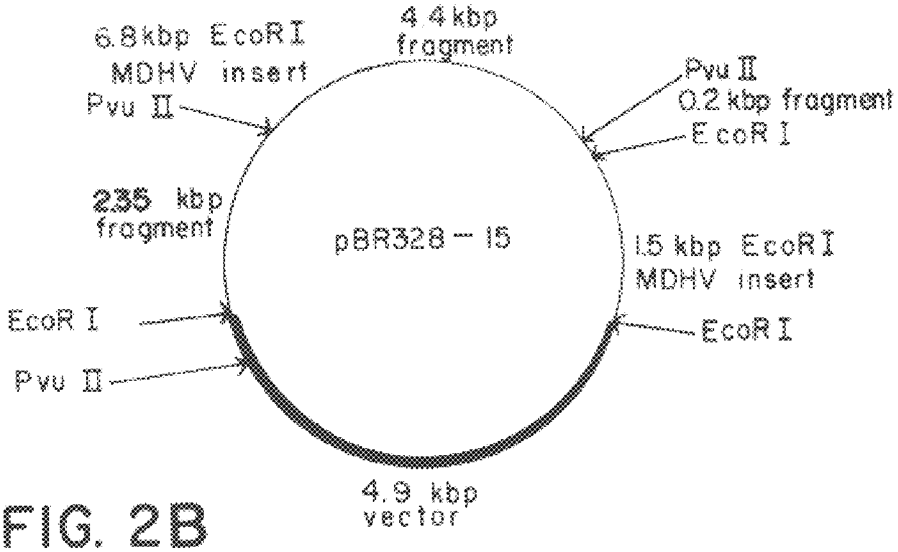
FIGS. 2A and 2B show a further analysis of clone pBR328-15 that selects MDHV-A mRNA.
Figure 2B:
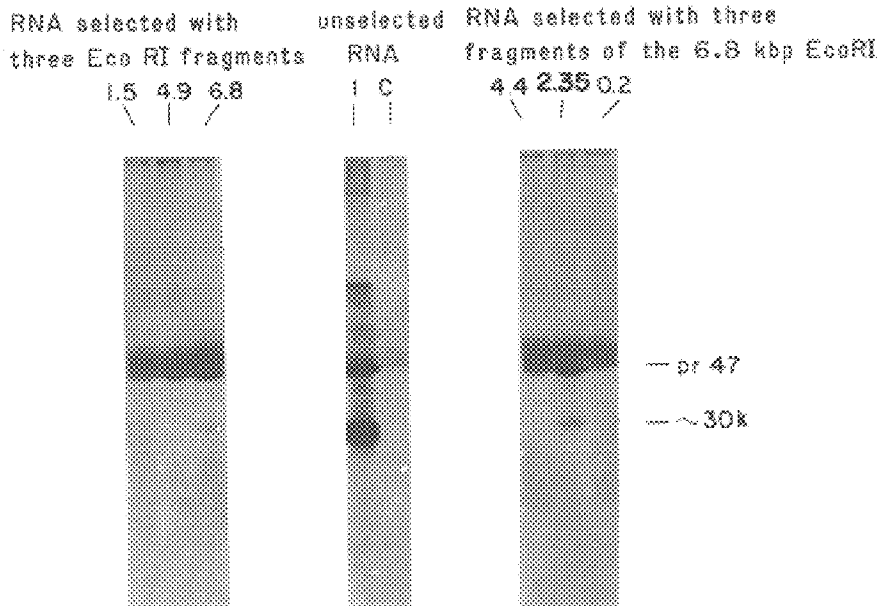

Clone pBR328-15 contains two MDHV Eco Rl fragments, a 6.8 kbp fragment and a 1.5 kbp fragment (FIG. 2A). When each of the two cloned MDHV DNA inserts and the 4.9 kbp vector DNA were tested for their ability to select MDHV-A mRNA, it was discovered that the 6.8 kbp MDHV Eco Rl fragment contained the genomic coding sequence for MDHV-A (FIG. 2B, left side). This is based on the presence of the dark band of pr47 just under the more gray background smear occurring in these gels. Once again the 30–36 k molecule is detected in the same lane. While these two bands are not as apparent on the left side of FIG. 2B compared to previous and subsequent data, apparently due to less than optimal efficiency of selection and/or translation this one time, the correctness of these data is confirmed by their repetition and extension in the next experiment and subsequent experiments.

Upon further digestion with the restriction enzyme Pvu II, the 6.8 kbp fragment could be divided into three subfragments of 0.2, 2.35, and 4.4 kbp as mapped and illustrated in FIG. 2A. When these three fragments were isolated and used for hybrid-selection, the results in the right side of FIG. 2B were obtained. It is clear that the fragment which contains the coding region for MDHV-A is the terminal Eco Rl-Pvu II 2.35 kbp fragment (FIG. 2B). Northern blot analysis with the same three subfragments confirmed this localization of the MDHV-A gene, only the 2.35 kbp subfragment detected the MDHV-A mRNA, which is described below. Note that the mRNA for the 30–36 kd protein was also hybrid-selected by this small fragment.

Figure 3:
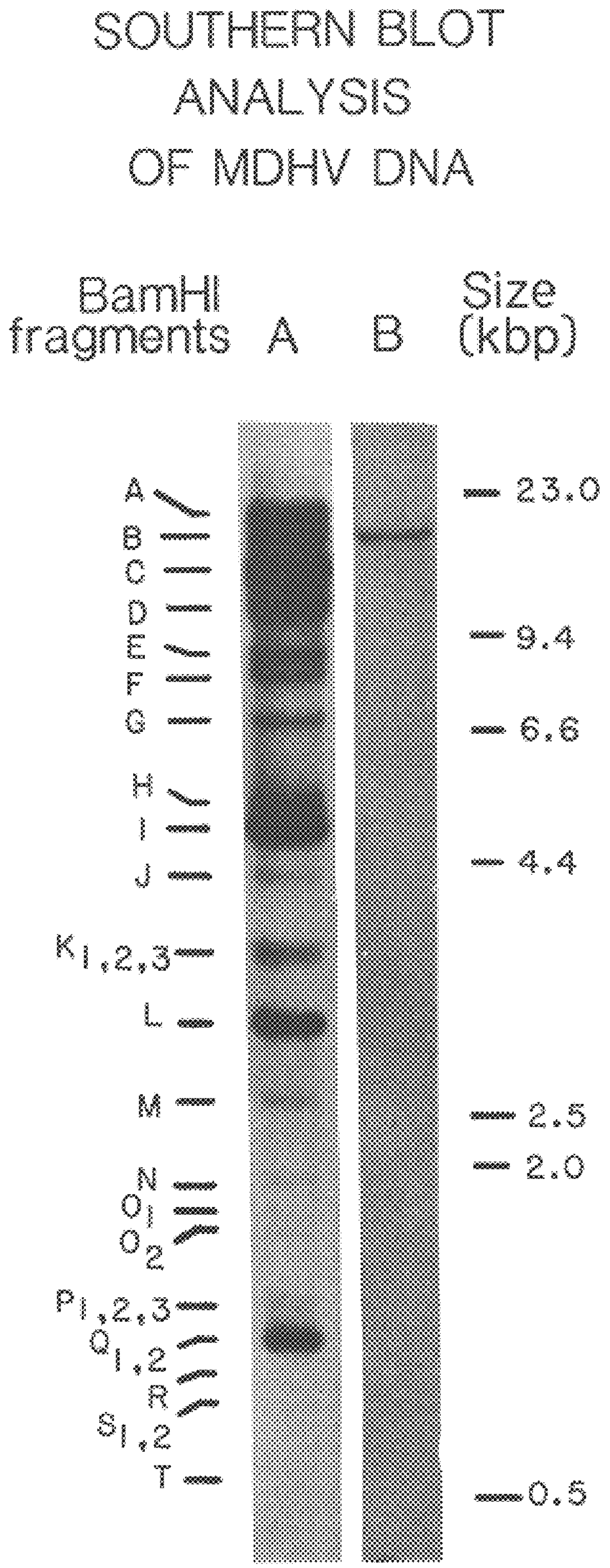
FIG. 3 shows a southern blot analysis of Bam Hl-digested MDHV DNA probed with either (A) total MDHV DNA or (B) the 2.35 Eco Rl-Pvu II MDHV DNA restriction fragment containing the MDHV-A coding region. DNA isolation, restriction enzyme digestion, blotting, hybridization, and nick-translations were performed as described in the specification. The hybridization was specific for Bam Hl B fragment (18.3 kbp).

Since the 2.35 kbp subfragment that selects for the A antigen mRNA lies at the end of the pBR328 6.8 kbp Eco Rl fragment, it is possible that the entire gene for DHV-A is not encoded on this fragment. Since no other pBR328 clone was able to select message for the A antigen (FIG. 1B), it was necessary to obtain a more complete library of the MDHV genome for further gene identification studies. Fortunately, during the course of this study a nearly complete library was created (Fukuchi, K., M. Sudo, Y. S. Lee, A. Tanaka, and M. Nonoyama. J. Virol. 51:102–109 (1984)) and the Bam Hl DNA fragments were made available to us. In order to identify the Bam Hl fragment which corresponds to the MDHV pBR328 clone that we have identified as encoding MDHV-A, a Bam Hl digest of purified MDHV DNA was separated by gel electrophoresis, Southern blotted, and used to hybridize with a probe of the labeled 2.35 kbp Eco Rl-Pvu II subfragment of pBR328-15. As can be seen in FIG. 3, only the Bam Hl fragment B contained the sequence corresponding to the 2.35 kbp Eco Rl-Pvu II subfragment.

In order to determine where in the large (18.3 kbp) Bam Hl fragment B the genetic information of the 2.35 kbp Eco Rl-Pvu II sub fragment lies, fragment B was first digested with several restriction endonucleases and physically mapped (FIG. 4). The restriction digests were gel electrophoresed, Southern blotted and hybridized to a radioactive probe of the Eco Rl-Pvu II 2.35 kbp subfragment of pBR328-15 (FIG. 2A). Following this, the blot was then hybridized to a radioactive probe of complete 6.8 kbp Eco Rl fragment. The combined information served to determine the orientation and directionality of the 6.8 kbp fragment and its 2.35 kbp subfragment in Bam HI B. As is seen in the resultant map (FIG. 4), the 2.35 kbp Eco RI-Pvu II subfragment lies in the center of Bam Hl B fragment. Thus the adjacent sequences are available to determine if any of the MDHV-A gene lies adjacent to the 2.35 kbp Eco Rl-Pvu II subfragment known to contain at least part of the gene.

Figure 4A:
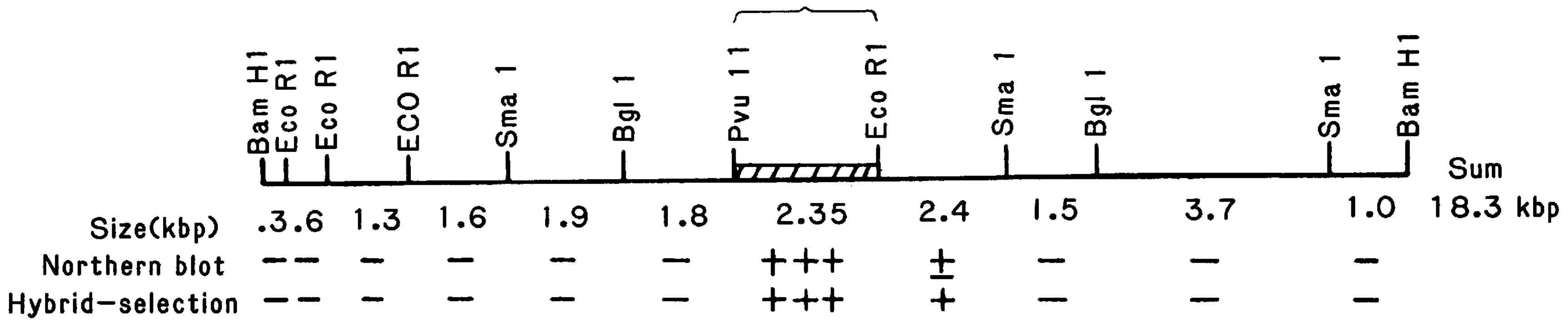
FIG. 4A is a map of Bam Hl B fragment showing orientation and approximate position of the MDHV-A antigen coding region as determined by both hybrid-selection and northern blot analysis. Both hybrid-selection and Northern and Southern blot analysis was performed as described in the specification. The 2.35 kbp fragment containing the MDHV-A coding region is in the middle of the fragment.

In order to delineate the extent of the A antigen gene in the Bam Hl B fragment, the other restriction fragments of Bam Hl B shown in FIG. 4A were isolated and used to hybrid-select the MDHV-A mRNA. From these studies it appears that a 2.4 kbp Eco Rl-Sma l subfragment adjacent to the 2.35 kbp Eco Rl-Pvu II subfragment was also able to hybrid-select the MDHV-A mRNA (FIG. 4A), although this selection was not as strongly positive as with the 2.35 kbp Pvu II-Eco Rl subfragment. However, other than these two subfragments, no other DNA sequences in the entire Bam Hl B fragment were able to hybrid-select MDHV-A mRNA, thereby delineating the approximate limits of the A antigen coding region.

To complete this initial analyses of the MDHV-A gene Northern blot analysis was performed using the same RNA preparations used above for hybrid selection. In this case the 2.35 kbp Pvu II-Eco Rl fragment, the one most strongly positive in hybrid-selection was nick-translated and used as a probe. It detected an mRNA band migrating just below the position of 18S RNA marker (FIG. 5), a size of approximately 1.8 kbp. When all the other subfragments of the Bam Hl B fragment were used as probes for Northern blot analysis none of them detected the same 1.8 kbp mRNA on short exposure of the gel to X-ray film. The 2.4 kbpEcoRl-Smal fragment was very weakly positive in detecting the same mRNA, and then only upon long exposure (FIG. 4).

DISCUSSION

The purpose of this invention was to identify the location of the coding region for MDHV-A antigen within the MDHV genome. Initially the MDHV-A gene was identified within the library of pBR328 clones (FIG. 1) previously developed and studied in these laboratories (Gibbs, C., K. Nazerian, L. F. Velicer, and H. J. Kung, Proc. Natl. Acad. Sci. USA 81:3365–3369 (1984)). The gene was first localized on a 2.35 kbp subfragment of an approximately 6.8 kbp clone temporarily designated pBR328-15 (FIG. 2) herein. The DNA fragment carrying the MDHV-A gene is actually the one designated M in other published work using these clones (Gibbs, C., K. Nazerian, L. F. Velicer, and H. J. Kung, Proc. Natl. Acad. Sci. USA 81:3365–3369 (1984)).

Further work with the MDHV-A gene in this clone seemed inadvisable for two reasons: 1) location of the 2.35 kbp subfragment near one end of the larger fragment (FIG. 2) means it was possible that the entire gene was not present on the fragment, and 2) the pBR328 library contains only 30% of the MDHV genome. Thus, since none of the other pBR328 clones hybrid-selected MDHV-A the real possibility existed that not all of its gene was available. Fortunately at this time Fukuchi et al (Fukuchi, K., M. Sudo, Y.-S. Lee, A. Tanaka, and M. Nonoyama, J. Virol. 51:102–109 (1984)) published a paper on the structure of the MDHV genome using the GA strain, the same one used in our original cloning studies (Gibbs, C., K. Nazerian, L. F. Velicer, and H. J. Kung, Proc. Natl. Acad. Sci. USA 81:3365–3369 (1984)). These authors (Fukuchi, K., M. Sudo, Y.-S. Lee, A. Tanaka, and M. Nonoyama, J. Virol. 51:102–109 (1984)) presented Bam Hl, Bgl I and Sma l restriction endonuclease maps of MDHV DNA. They had successfully cloned 27 of the 29 Bam Hl fragments and these were then made available for study by others. Since their Bam Hl library constituted nearly 100 percent of the MDHV genome and was well mapped it seemed wisest to use it as a potential source of the entire MDHV-A gene for all future studies.

Initial localization of the MDHV-A gene in the Bam HI library was by Southern blot analysis with the 2.35 kbp Eco Rl-Pvu II subfragment of the pBR328 clone (FIG. 3) used as a probe of the entire set of Bam Hl fragments. Clearly the MDHV-A genetic material in the 2.35 kbp subfragment hybridized only with the 18.3 kbp Bam Hl fragment B (FIG. 3). Upon further restriction mapping and hybrid-selection analysis it was found that the MDHV-A coding region lies on a 4.6 Pvu II-Sma l fragment found within the larger Bam Hl B fragment (FIG. 4). Because early mapping studies revealed an Eco Rl site this fragment can be subdivided into a 2.35 kbp Eco Rl-Pvu II fragment, and a 2.4 kbp Eco Rl-Sma 1 fragment, both of which can hybrid-select MDHV-A mRNA. However, the extent of selection is much greater with the former than with the latter fragment (FIG. 4A). Nevertheless these data appear to confirm the validity of our original concern that the 2.35 kbp Eco Rl-Pvu II subfragment of the pBR328-15 clone might not have contained the entire gene. However the weak hybrid-selection with the 2.4 kbp Eco Rl-Sma I fragment suggests that it contains only a very small piece of the MDHV-A gene, if any at all, a conclusion consistent with the very weak positive results obtained with the same fragment upon Northern blot analysis with long exposure of the X-ray film (FIG. 4). However it is now believed that these weak results are only due to a read-through during transcription of the gene. Nuclease Sl protection experiments were conducted in an attempt to determine more precisely the extent of the MDHV-A gene on the 2.4 kbp Eco RI-Sma I fragment and it was not found there. Furthermore DNA sequencing studies will include this fragment as well as to determine if it contains part of the MDHV-A gene's open reading frame. However, because of the inability of the other surrounding subfragments to hybrid-select MDHV-A mRNA, or detect the mRNA upon Northern blot analysis, it is assumed that the complete A antigen coding region has been identified within the center of the Bam Hl B fragment. This fragment is in the right handed half of the unique long region of the virus genome based on the map of Fukuchi et al. (Fukuchi, K., M. Sudo, Y.-S. Lee, A. Tanaka, and M. Nonoyama., J. Virol. 51:102–109 (1984)).

Based on the size of MDHV-A's unglycosylated precursor polypeptide, pr47 (Isfort, R. J., R. A. Vrable, K. Nazerian, H.-J. Kung, and L. F. Velicer. Gene identification and molecular characterization of the Marek's disease virus A antigen, p. 130–147. In B. W. Calnek and J. L. Spencer (eds.), Proc. Int. Symp. Marek's Dis. The American Association of Avian Pathologists, Inc, Kennett Square, Pa. (1984); Isfort, R. J., R. A. Stringer, H. J. Kung, and L. F. Velicer, J. Virol. 57:464–474 (1986), FIG. 1 and FIG. 2), it is possible to predict that its mRNA should be approximately 1.7 kbp. Detection of MDHV-A mRNA of 1.8 kbp is consistent with this prediction, and the small size difference suggests that splicing is minimal if it occurs at all.

So far, a function for the A antigen has not been found. Its possible role(s) in immunoprevention and/or immunosuppression were mentioned in the introduction. Possibly it is not needed for virus growth since A antigen negative strains are known and are able to propagate well in tissue culture. However more rigorous proof that these strains are truly negative may be called for. Recently however, the A antigen has been implicated as having a role in host immunoevasion, possibly as a function of its extensive secretion (Isfort, R. J., R. A. Stringer H. J. Kung, and L. F. Velicer, J. Virol. 57:464–474 (1986)).

DETAILED ANALYSIS OF THE MDHV-A GENE

The MDHV-A gene containing 2.35 kbp EcoRI-Pvu II segment of the MDHV Bam HI B fragment was subcloned into the plasmid pUC19 to generate plasmid p19MDA2.35. This plasmid was deposited Mar. 11, 1987 under the terms of the Budapest Treaty with the American Type Culture Collection 10801 University Boulevard, Manassas, Va. 20110-2209. The culture will be available to all who request it upon issuance of a patent as ATCC 40312. This subclone has been used to construct detailed maps of restriction enzyme cleavage sites within the 2.35 kpb MDHV fragment. The 2.35 kbp fragment is cut at least once by the following restriction enzymes: Bgl II, EcoRI, EcoRV, Kpn I, Dra I, Dde I, Nco I, Ssp I, Spe I, and Taq I.

To unambiguously determine the orientation of the MDHV-A gene a combination of Northern blotting and nuclease protection analyses was employed. The 2.35 kbp EcoRI-Bam HI fragment of p19MDA2.35 was subcloned into the multiple cloning site (MCS) of plasmid pGem4 (Promega Biotech, Madison, Wis.). This placed the 2.35 kbp fragment between opposing SP6 and T7 RNA polymerase promoter sequences. Linearized plasmid DNA was used with either SP6 and T7 polymerase to direct the transcription of radioactively labeled complementary RNAs from the 2.35 kbp fragment. These labeled RNAs were used to probe Northern blots of MDHV-infected cell mRNA. In this system, only that RNA probe which is identical to the actual MDHV coding strand will hybridize to MDHV-A mRNA. This same system can be used as detailed below to generate smaller $^{32}P$ labeled RNA probes (length determined by choice of linearizing enzyme) for use in a nuclease protection analysis using RNase A and RNase T1 to specifically degrade unprotected RNA probe. In Northern blots only the $^{32}P$ labeled SP6 generated probe hybridized to MDHV-A mRNA immobilized on nitrocellulose, indicating that the MDHV-A gene was transcribed in the direction shown in FIG. 4B. These results were supported by Sl nuclease analysis using DNA probes (corresponding to I and II of FIG. 4B). Plasmid p19MDA2.35 was digested with Bgl II and radioactively labeled with polynucleotide kinase and ($-^{32}p$) ATP. Further cleavage with EcoRI and Bam HI generated probes I and II of FIG. 4B. Since these probes were labeled on different strands, only that strand which was complementary to the MDHV-A mRNA would hybridize to MDHV-A mRNA and be protected from Sl nuclease digestion. Consistent with the results from Northern blotting with SP6 and T7 polymerase generated RNA probes, only probe I was protected. Furthermore two species of probe I were protected in the above experiment, a major species of approximately 530 nucleotides and a minor species of 450 nucleotides thus indicating two potential transcription initiation sites within the Bam HI-Bgl II fragment, as indicated by solid arrows in FIG. 4B. The data from these experiments is being used to prepare smaller probes for additional Sl nuclease protection and primer extension experiments. The combination of Sl, primer extension, and DNA sequence analyses will allow precise localization of the MDHV-A gene transcription start site(s).

Figure 4B:
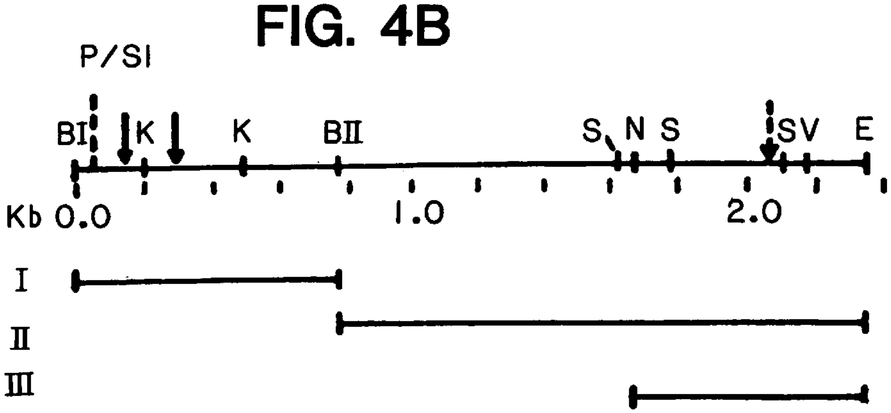
FIG. 4B is a fine structure mapping of the MDHV-A gene. The entire MDHV-A coding sequence of approximately 1.8–1.9 kbp in size (between the solid arrows and broken arrow) has been localized within the 2.35 kbp Pvu II-EcoRI segment of the MDHV Bam HI B fragment. Orientation and limits were determined by a combination of Sl nuclease, Northern blotting, and RNAse A/$T_1$ protection experiments using probes I–III. Sl nuclease assays (using probe I) indicate two major transcription initiation sites (solid arrows). RNase A/$T_1$ protection studies using SP6 generated RNA probes II and III were used in combination with Sl nuclease analysis to map the 3' end of the MDHV-A coding sequence (dashed arrow). Restriction enzymes used in subcloning and generation of probes were: BamHI (BI), Bgl II (BII), Kpn I (K), Ssp I (S), Nco I (N), EcoRV (V), EcoRI (E), Pvu II (P), and Sma I (SI).
Figure 5:
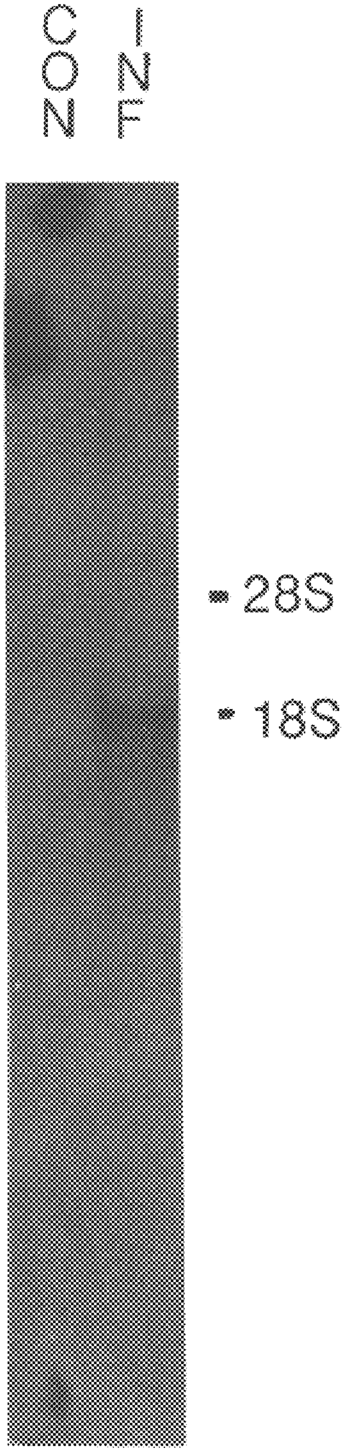
FIG. 5 shows a northern blot analysis of control and infected total cellular RNA using the 2.35 Eco Rl-Pvu II fragment as a nick-translated probe for hybridization. A total of 10 micrograms of RNA was loaded per lane and electrophoresed, blotted and probed as described in the specification. The exposure was for 1 hour. The messenger RNA of A antigen is about 1.8–1.9 kbp in size.

The MDHV-A gene's 3' end has been mapped approximately 367 nucleotides 5' of the EcoRI site (FIG. 4B, dashed arrow) by RNase A/T1 protection analysis using SP6 generated RNA probes (probes II and III, FIG. 4B). Once again location was further refined by traditional Sl nuclease protection analysis using a probe which extends from NcoI to EcoRV. The gene's orientation and limits suggest that the small amount of MDHV-A mRNA hybrid-selected by the 2.4 kbp EcoRI-Sma I segment of the Bam HI B fragment (FIG. 1) may be due to read-through during transcription of the gene.

This invention is extremely important to the MDHV system in three ways: 1) this is the first gene identified and cloned in this system, and 2) the means now exist to use modern approaches of recombinant DNA technology to study and use this late gene and its glycoprotein product. It is now known MDHV-A is a late protein based on phosphonacetic acid studies (L. F. Velicer, unpublished data). Thus these current studies should shed much light on the nature of a gene for a unique late glycoprotein antigen that is rapidly secreted from DEF cells, but may also have a membrane component (Isfort, R. J., R. A. Stringer H. J.Kung, and L. F. Velicer. J. Virol. 57:464–474 (1986). As the invention progresses it is expected more will be learned about the nature of an oncogenic herpesvirus encoded antigen that may be involved in immunoprevention, immunosuppression and/or possible immunoevasion.

The MDHV-A gene has a significant usefulness for diagnostic purposes in two different ways. First, the gene itself can be used directly for hybridization-based diagnostics to detect Marek's disease herpesvirus in birds, since it is also present in pathogenic Marek's disease herpesviruses. For example, as broilers are shipped to market at an earlier age infected birds might arrive for slaughter before lesions appear (the basis for condemnation) and the poultry industry may need a rapid diagnostic technique to screen flocks for infection.

Also when recombinant DNA vaccines are on the market it will be necessary to differentiate those of an infectious nature (one of many vaccine forms under consideration) from the wild type virus that is spread in nature, especially for legal and environmental reasons. In this case the MDHV-A gene is useful to modify slightly (e.g., insert some sort of distinctive marker DNA sequence) so the recombinant vaccine virus can be readily identified.

The MDHV-A gene is useful in the development of sensitive and specific ELISA based diagnostics of an immunologic nature, in one of two ways, based on production of MDHV-A in cells transfected with this gene and producing the antigen. The antigen can be used directly in an ELISA assay to detect antibody in the sera of chickens. It could also be used indirectly to produce highly specific antibody (monoclonal and polyclonal) that can be used on the ELISA assay to detect the antigen in infected birds. The A antigen is of special interest in terms of diagnostic sensitivity because it is the most prominent antigen made during infection, and it is also the one the bird reacts to most extensively. Thus it would be our first choice for diagnostic purposes.

On top of all else MDHV-A has a signal peptide which facilitates the antigen's secretion from cells. The part of the gene encoding its signal peptide may be extremely valuable in the production of the other antigen(s). If this part were put onto the gene encoding another antigen that is not normally secreted, the other antigen might now be secreted. This would be an extremely valuable feature in the production and purification of this other antigen in eucaryotic expression vectors. There is also a promoter which can be used to promote the expression of unrelated genes. Thus the signal peptides and promotors are used as regulatory elements for other genes.

It is intended that the foregoing description be limited only by the hereinafter appended claims.

What is claimed is:

1. A purified EcoRl-PvuII restriction subfragment having a length of about 2.35 kbp in a BAM HI B restriction fragment of Marek's disease herpesvirus genome wherein the subfragment encodes A antigen precursor.

2. A plasmid comprising the subfragment of claim 1.

3. An expression vector comprising the subfragment of claim 1.

4. A cell with an expression vector comprising the subfragment of claim 1 which cell expresses A antigen precursor because of the presence of the subfragment.

5. The plasmid of claim 2 wherein the plasmid is pUC19.

6. A gene fragment encoding A antigen precursor of Marek's disease herpesvirus which is an insert in plasmid pUC19 deposited as ATCC 40312.

7. A purified gene fragment coding for Marek's disease herpesvirus A antigen precursor which is a EcoRl-PvuII endonuclease insert in pUC19 deposited as ATCC 40312.

8. A method for isolating the gene coding for A antigen precursor from DNA of Marek's disease herpesvirus which comprises:

(a) digesting a BAM HI B fragment of the DNA with EcoRl-PvuII endonucleases to provide a subfragment having a length of about 2.35 kbp wherein the subfragment encodes the A antigen precursor; and (b) isolating the subfragment, which codes for the A antigen precursor by hybrid selection with MDHV-A mRNA.

* * * * *